United States Patent
Aldrich

(12) 
(10) Patent No.: US 6,615,064 B1
(45) Date of Patent: Sep. 2, 2003

(54) NON-INVASIVE BLOOD COMPONENT ANALYZER

(75) Inventor: Thomas K. Aldrich, Pelham, NY (US)

(73) Assignee: Essential Medical Devices, Inc., Pelham, NY (US)

(*) Notice: Subject to any disclaimer, the term of this patent is extended or adjusted under 35 U.S.C. 154(b) by 0 days.

(21) Appl. No.: 09/514,789

(22) Filed: Feb. 28, 2000

Related U.S. Application Data

(63) Continuation-in-part of application No. 09/157,453, filed on Sep. 21, 1998, now Pat. No. 6,064,898.

(51) Int. Cl.7 .................................................. A16B 5/00
(52) U.S. Cl. ........................ 600/316; 600/322; 600/323; 600/328
(58) Field of Search ................................. 600/310, 315, 600/316, 319, 322, 323, 326, 329, 330, 335, 336, 407, 473, 476

(56) References Cited

U.S. PATENT DOCUMENTS

| | | |
|---|---|---|
| 3,958,560 A | 5/1976 | March |
| 4,167,331 A | 9/1979 | Nielson ........................ 356/39 |
| 4,194,217 A | 3/1980 | van den Bosch ............. 358/93 |
| 4,394,572 A | 7/1983 | Wiber ......................... 250/239 |
| 4,407,290 A | 10/1983 | Wilber |
| 4,621,643 A | 11/1986 | New et al. |
| 4,653,498 A | 3/1987 | New et al. |
| 4,655,225 A | 4/1987 | Dahn et al. |
| 4,700,708 A | 10/1987 | New et al. |
| 4,714,080 A | 12/1987 | Edgar |
| 4,770,179 A | 9/1988 | New et al. |
| 4,819,752 A | 4/1989 | Zelin |
| 4,882,492 A | 11/1989 | Schlager ...................... 250/346 |
| 4,909,259 A | 3/1990 | Tehrani |
| 4,934,372 A | 6/1990 | Coremn et al. |
| 4,997,769 A * | 3/1991 | Lundsgard ................... 436/66 |
| 5,009,230 A | 4/1991 | Hutchinson |
| 5,028,787 A | 7/1991 | Rosenthal et al. .......... 250/341 |

(List continued on next page.)

FOREIGN PATENT DOCUMENTS

| | | |
|---|---|---|
| DE | 4238641 | 5/1994 |
| EP | 0208201 | 1/1987 |
| EP | 0374190 | 6/1990 |
| EP | 0536304 | 4/1993 |
| SU | 888931 | 12/1981 |

OTHER PUBLICATIONS

Arnold MA. Noninvasive blood glucose monitoring. *Curr Opinion Biotech* 7:46–9, 1996.

Cavinato AG, Mayes DM, Ge ZH, Callis JB. Noninvasive method for monitoring ethanol in fermation process using fiberoptic near–infrared spectroscopy. *Anal Chem* 62:1977–82, 1990.

Hall JW, Pollard A. Nea–infrared spectroscopic determination of serum total proteins, albumin, globulins, and area. *Clin Biochem* 26:463–90, 1993.

Hall et al., Near infrred Spectrophotometry: A New Dimension in Clinical Chemistry. *Clin. Chem* 38/9, 1623–31 (1992).

Hanning CD, Alexander–Williams JM. Pulse Oximetry: a practical review. *BMJ* 311:367–70, 1995.*

(List continued on next page.)

Primary Examiner—Eric F. Winakur
(74) Attorney, Agent, or Firm—Patterson, Belknap, Webb & Tyler LLP

(57) ABSTRACT

A non-invasive blood component analyzer using spectrophotometry, with systole/diastole corrections for tissue absorbance, and with built-in monitoring of light path length to allow its accurate use in subjects with widely varying finger size and/or varying pulse amplitude. Blood components that are able to be analyzed include oxyhemoglobin, total hemoglobin, bilirubin, glucose, hormone levels and a variety of drugs.

1 Claim, 10 Drawing Sheets

U.S. PATENT DOCUMENTS

| | | | |
|---|---|---|---|
| 5,086,229 A | | 2/1992 | Rosenthal et al. .......... 250/341 |
| 5,101,825 A | | 4/1992 | Gravenstein et al. |
| 5,137,023 A | | 8/1992 | Mendelson et al. |
| 5,139,025 A | * | 8/1992 | Lewis et al. ............... 600/477 |
| 5,187,672 A | * | 2/1993 | Chance et al. .............. 600/407 |
| 5,285,782 A | * | 2/1994 | Prosser |
| 5,297,548 A | | 3/1994 | Pologe |
| 5,313,941 A | | 5/1994 | Braig et al. |
| 5,355,880 A | * | 10/1994 | Thomas et al. |
| 5,360,004 A | | 11/1994 | Purdy et al. |
| 5,372,136 A | | 12/1994 | Steuer et al. |
| 5,413,100 A | * | 5/1995 | Barthelemy et al. |
| 5,435,309 A | * | 7/1995 | Thomas et al. |
| 5,490,505 A | * | 2/1996 | Diab et al. |
| 5,491,341 A | * | 2/1996 | McCaul et al. ............. 250/343 |
| 5,503,148 A | * | 4/1996 | Pologe et al. ............... 600/323 |
| 5,522,388 A | | 6/1996 | Ishikawa et al. |
| 5,553,615 A | | 9/1996 | Carim et al. |
| 5,636,633 A | | 6/1997 | Messerschmidt et al. |
| 5,638,816 A | * | 6/1997 | Kiani-Azarbayjaney et al. |
| 5,655,530 A | | 8/1997 | Messerschmidt et al. |
| 5,722,398 A | | 3/1998 | Ishihara et al. |
| 5,741,213 A | | 4/1998 | Kouchi et al. .............. 600/310 |
| 5,769,076 A | | 6/1998 | Mackawa et al. |
| 5,823,951 A | | 10/1998 | Messerschmidt et al. ... 600/322 |
| 5,842,979 A | * | 12/1998 | Jarman ........................ 600/322 |
| 5,869,971 A | | 2/1999 | Sherman ..................... 324/439 |

OTHER PUBLICATIONS

Heise HM, Marbach R, Koschinsky T, Gries FA. Noninvasive blood glucose sensors base on near infrared spectroscopy. *Artif Organs* 18:439–47, 1994.*

Merschbrock U., et al., Fast wavelength scanning relectance spectrophotometer for noninvasive determination of hemoglobin oxygenation in human skin. *Int J Microcire Clin Exp* Sep.–Oct. 1994; 14(5):274–81.

Rao, V.M. et al., Noninvasive diagnostic imaging in hemoglobinopathies. *Hematol Oncol Clin North Am* Jun. 1991; 5(3):517–33.

Takatani S, Eheung P.W., Ernst E.A., A noninvasive tissue reflectance oximeter. An instrument for measurement of tissue hemoglobin oxygen saturation in vivo. *Ann Biomed Eng* 1980; 8(1):1–15.

Yamakoshi K., Tanaka S., Shimazu H. Electrical admittance cuff for noninvasive and simultaneous measruement of haematocrit arterial pressure and elasticity using volume–oscillometric method. *Med Biol Eng Comput* Jul. 1994; 32(4 Suppl):S59–107.

Gravenstein, D., S. Lampotang et al. (1994). Noninvasive hemoglobinometry, *Anethesiology* 81(3A): A576. (Poster).

D. Li, Y. Wang, D. Waight., Blood oxygen saturation assessment in vivo using T2* estimation. *MRM* 1998, 39:685–690.

Steuer, R. R., D. H. Harris, et al. (1991). Evaluationof a noninvasive hematocrit monitor: a new technology. *Am Clin Lab* 10(6): 20–2.

Yamakoshi, K. L. H. Shimazu, et al. (1980). Noninvasive measurement of hematocrit by electrical admittance plethysmography techniue. IEEE *Trans Blomed Eng* 27(3): 156–61.

Mancini E, Santoro A, Sporgano M, Paolini F, Rossi M, Zucchelli P. Continuous on–line optical absorbance recording of blood volume changes during hemodialysis. *Artif Organs* 17:691–4, 1993.

Linder et al. Noninvasive Determination of Neonatal Hyperbilirubinemia: Standardization for Variation in Skin Color, *Am J Perinatology* 11:223–5, 1994.

Lindberg et al. Pulse Oximetry—Clinical implications and recent technical developments. *Acta Anaesthesiologica Scandinvavica.* 39 (1995).

Mahoney et al. Measurement of Caraboxyhemoglobin and Total Hemoglobin by Five Specialized Spectrophotometers (Co–oximeters) in Comparison with Reference Methods. *Clin Chem* 39/8, 1693–1700. (1993).

McDonald OL, Watts MT. Use of commercially prepared control sera as quality control materials for spectrophotometric bilirubin determinations in amniotic fluid. *Am J Clin Pathol* 84:51307, 1985.

Mendelson Y. Pulse oximetry: theory and applications for noninvasive monitoring. *Clinical Chemistry* 38: 1601–7, 1992.

Pickup, J. Developing Glucose Sensors for in vivo use. *Trends in Biotech,* 1993 11:285–91.

Robinson MR, Eaton RP, Haaland DM, Koepp GW, Thomas EV, Stallard BR, Robinson PL. Noninvasive glucose monitoring in diabetic patients: a preliminary evaluation. *Clin Chem* 38:1618–22, 1992.

Ruchala PL, Siebold L. Stremsterfer K. Validating assessment of neonatal jaundice with transcutaneous bilirubin measurement. *Neonatal Network* 15:33–7, 1996.

Sanchez–Carillo Cl. Ramirez–Sanchez T de J, Zambrana–Castaneda M, Selwyn BJ. Test of a noninvasive instrument for measuring hemoglobin concentration. *Intl J Technology* 5:659–67, 1989.

Severinghaus JS and Kelleher JF. Recent developments in pulse oximetry, *Anesthesiology* 76:1018–38, 1992.

Siek TJ, Rieders F. Determination of carboxyhemoglobin in the presence of other blood hemoglobin pigments by visible spectrophotometry. *J Forensic Sci* 29:39–54, 1984.

Vegfers et al. Carbosyhaemoglobinaemia and pulse oximetry. *Brit J Anaesth* 66:625–6, 1991.

Yamamoto Y. Oberg PA. Measurement of digital bood flow using the laser Doppler, impedance, and strain gauge methods. *Med Biol Eng Comput* 28:113–8, 1990.

Zeller H. Novak P. Landgraf R. Blood Glucose measurement by infrared spectoscopy. *Intl J. Artif Org* 12:12–35, 1989.

Zijistra et al. Performance of an automated Six–Wavelength Photometr (Radiometer OSM3) for Routine Measurement of Hemoglobin Donestives. *Clin Chem* 34/1 149152 (1988).

* cited by examiner

NON-INVASIVE BLOOD COMPONENT ANALYZER

This application is a continuation-in-part of U.S. application Ser. No. 09/157,453, issued as U.S. Pat. No. 6,064,898, filing date Sep. 21, 1998.

BACKGROUND OF THE INVENTION

1. Field of the Invention

The present invention is directed to a non-invasive device and method for analyzing the concentration of blood components, including oxygen saturation, bilirubin, hemoglobin, oxyhemoglobin, glucose, hormones and a variety of drugs.

2. Description of the Prior Art

Analysis of blood components is regularly required in hospitals, emergency rooms, doctors' offices, and in patients' homes (in the case of blood glucose analysis for example), for a variety of diagnostic purposes and to monitor therapy. In most cases, blood is obtained by venipuncture or finger prick, which raises small but important concerns regarding pain and the potential for transmission of infectious disease, such as viral hepatitis and human immunodeficiency virus (HIV) infection. The pain associated with blood drawing often inhibits patient compliance with prescribed blood testing, leading to potentially dangerous consequences of undiagnosed disease. Also, the need for trained technicians to draw and handle blood contributes to the high cost of medical care. Furthermore, blood testing procedures take time, which often delays diagnosis. Finally, for practical reasons, blood testing can be done only at intervals, providing only "snap-shot" data regarding the blood component of interest. Under some circumstances, as for example during the assessment of blood losses due to gastrointestinal hemorrhage or during the assessment of the response to hemodialysis, to the treatment of diabetic ketoacidosis, or to the treatment of acute intoxications, it would be desirable to monitor the concentration of one or more blood components continuously.

Blood tests are often performed in "panels;" that is, a number of tests is run on a single drawn blood sample. However, there are also clinical circumstances in which only a single or a small number of tests are required, or when a single test must be performed repeatedly over time. In such cases, noninvasive tests that do not require blood drawing would be particularly useful.

An example of a currently available noninvasive test is pulse oximetry, which measures the adequacy of saturation of arterial blood hemoglobin with oxygen. Mendelson Y., *Pulse Oximetry: Theory and Applications for Noninvasive Monitoring, Clinical Chemistry* 38:1601–7, 1992; Hanning C D, Alexander-Williams J M., *Pulse Oximetry: A Practical Review, BMJ* 311:367–70, 1995; Severinghaus J W and Kelleher J F., *Recent developments in pulse oximetry, Anesthesiology* 76:1018–38, 1992; Corenman et al., U.S. Pat. No. 4,934,372; Edgar et al., U.S. Pat. No. 4,714,080; Zelin, U.S. Pat. No. 4,819,752; and Wilber, U.S. Pat. No. 4,407,290. Oximeters have become indispensable for screening patients for life-threatening hypoxemia and for monitoring patient safety during procedures such as surgery and childbirth. Oximeters reliably report the relative arterial oxygen level (percent of the maximum that can be carried by the available hemoglobin), but they cannot measure absolute oxygen content of the blood, because their readings are independent of hemoglobin concentration.

In pulse oximeters, light produced by two light-emitting diodes (LEDs) at approximately 660 nm (red) and 940 nm (infrared) are alternately passed through the subject's finger, toe, or ear (or other well-perfused tissue), and the transmitted light is measured by a rapidly-responding photodetector. The light that is not transmitted to the photodetector is absorbed by the finger or is scattered out of the range of the photodetector. The amount of absorbance depends on tissue density and the amount and character of the blood (venous and arterial) that is present in the light path. At each of the two wavelengths, the resulting time-varying measurement of light intensity for the wavelength, termed "photoplethysmography," is roughly inversely proportional to finger volume, which varies with the arterial pulse.

Changes in absorbance (A) are caused by changes in the amount of blood present in the light path, assumed to be primarily changes in the amount of arterial blood due to the arterial pulse. Because absorbance of oxy-hemoglobin differs for light at the two wavelengths, a ratio of change in absorbance of red to change in absorbance of infrared light can be used to measure oxy-hemoglobin percentage. In practice, transmittance ($T=10^{-A}$) is measured from each of the photoplethysmograms, absorbance ($A=\log 1/T$) is calculated, and the change in absorbance with the arterial pulse is calculated for each wavelength studied. A ratio of the two changing absorbances is then computed, and after inconsistent data points are discarded, the ratios are averaged to yield an average ratio of red/infrared absorbance change. The average ratio is then multiplied by a correction factor, which has been empirically determined for each instrument by comparison with oxy-hemoglobin levels measured by a co-oximeter in arterial blood samples in normal subjects with varying levels of oxyhemoglobin produced as a result of breathing gases with varying fractions of inspired oxygen ($FiO_2$).

Commercial pulse oximeters used to measure the amount of arterial blood oxygen saturation ($SaO_2$) are available from the following manufacturers: BCI International, Biochem International, Inc., Criticare Systems, Inc., Datascope Corp., Datex Instrumentation Corp., Gambro Engstrom A.B., Invivo Research, Inc., Kontron Instruments, Life Care International, Inc., MSA, Medical Research Laboratories, Minolta Camera Co., Ltd., Nellcor-Puritan-Bennett, Nippon Colin Co., Ltd., Nonin Medical Systems, Inc., Ohmeda, Inc., Palco Labs, PhysioControl, Respironics, Inc., Sensor Medics Corp., Siemens Medical Systems, Inc., Novametrics Medical Systems, Inc., Simed Corp. and Spectramed, Inc.

Pulse oximeters can be controlled with various software packages, including those made by EMG Scientific. Signal processing apparatus, such as that disclosed in U.S. Pat. No. 5,490,505, can be used to process the signals generated by a pulse oximeter.

Prior designs of pulse oximeters used to measure arterial oxygen saturation are well known. For example, U.S. Pat. No. 4,653,498 to New, Jr. et al. (1987) describes a display monitor for use with a pulse oximeter of the type wherein light of two different wavelengths is passed through body tissue, such as a finger, an ear or the scalp, so as to be modulated by the pulsatile component of arterial blood therein and thereby indicates oxygen saturation. Similarly, U.S. Pat. No. 4,621,643 (1986), U.S. Pat. No. 4,700,708 (1987) and U.S. Pat. No. 4,770,179 (1988), all to New, Jr. et al., describe disposable probes for use with pulse oximeters.

U.S. Pat. No. 5,810,723 to the same inventor as the instant application, which issued on Sep. 22, 1998 from copending application Ser. No. 08/759,582, is entitled Non-Invasive Carboxyhemoglobin Analyzer. In that patent an apparatus and method is disclosed which allows the non-invasive monitoring of a subject's carboxyhemoglobin level, thereby allowing the detection of possible carbon monoxide poisoning. The subject breathes oxygen to lower his reduced hemoglobin level to approximately 0%, thus allowing the detection and differentiation between oxy- and carboxyhemoglobin by modification of a conventional pulse oximeter.

Noninvasive monitors of bilirubin are also available, especially for following the course of neonatal jaundice. See Linder N, Regev A, Gazit G, Carplus M, Mandelberg A, Tamir I, Reichman B., Noninvasive determination of neonatal hyperbilirubinemia: standardization for variation in skin color; *Am J Perinatology* 11:223–5, 1994. Usually, the absorbance by a body part of light near the peak absorption of bilirubin is monitored. Bilirubinometers are generally calibrated by comparison with measured blood bilirubin in the infant to be monitored. Without such calibration, the varying amounts of tissue and blood in the light path limits the accuracy of the measurements. Thus, at least one blood sample is required.

Examples of other blood tests that are often done alone and/or must be repeated at frequent intervals include: blood hemoglobin or hematocrit measurements for patients with known or suspected anemia, actively hemorrhaging from disease or surgery, and/or undergoing transfusion therapy; glycosylated hemoglobin levels in diabetic patients to assist in assessing adequacy of blood glucose control: blood glucose levels in patients with diabetes or suspected hypoglycemia, for diagnosis of hyper- or hypo-glycemia or for monitoring the effectiveness of insulin or oral hypoglycemic therapy; thyroid hormone levels in persons with hyper- or hypothyroidism; ethanol levels in patients suspected of ethanol intoxication; and a variety of drug and drug metabolite levels (e.g. digoxin, theophylline, dilantin, morphine, benzodiazepines, anabolic steroids) in patients undergoing therapy or suspected of being intoxicated with such drugs.

Noninvasive monitors for glucose, ethanol, and other blood components have been suggested, but have not proven to be feasible, accurate, and/or economically viable. Zeller H, Novak P, Landgraf R, *Blood Glucose Measurement By Infrared Spectroscopy, Intl J Artif Org* 12:12–35, 1989. Examples include the device described by March in U.S. Pat. No. 3,958,560, which measures glucose in the cornea of the eye by determining the rotation of reflected polarized infrared light. Although it does not require blood drawing, March's technique is cumbersome and uncomfortable for patients and not suitable for routine monitoring.

The techniques of Hutchinson, U.S. Pat. No. 5,009,230; Dahne et al., U.S. Pat. No. 4,655,225; Mendelson et al., U.S. Pat. No. 5,137,023; Rosenthal et al., U.S. Pat. No. 5,028,787; Schlager et al., U.S. Pat. Nos. 4,882,492; 5,638,816, Kiani-Azarbayjany, et al.; and Purdy et al., U.S. Pat. No. 5,360,004 use near infrared light (<2.5 cm wavelength) to assess glucose or other blood components. All suffer from inaccuracies due to the relatively weak absorption bands of glucose in the near infrared spectrum, from overlapping absorption from water, proteins, or other blood components, and especially from varying amounts of blood and tissue in the optical path. Some improve their resolution by using pulsatile flow or displacement of blood as in Dahne et al., and Mendelson et al. to provide a subtractable background, but problems with varying and unknown blood path-length persist.

Braig et al., U.S. Pat. No. 5,313,941 describes a device employing midinfrared light to measure glucose or ethanol, with synchronization of measurements with the cardiac cycle in order to factor out contributions from components of the finger other than arterial blood. Although the use of systole/diastole comparisons help to limit the interfering influences of tissues other than blood, the accuracy of the described instrument also suffers from its inability to take light path length into account. The instrument is calibrated by comparison with blood samples in volunteer subjects, but subjects with varying finger size and/or varying finger blood volume would yield varying results.

Kiani-Azarbayjany, et al., U.S. Pat. No. 5,638,816, describes a device that produces larger-scale oscillations in tissue blood volume than occur with arterial pulses and analyzes the variations in near infrared absorbances during such oscillations to measure glucose, various species of hemoglobin, and drug concentrations in blood. However, Kiani fails to account for or measure change in light path length. Kiani's device solves the problem of an unknown light path length by normalizing the measurement of the blood constituent of interest, e.g. glucose, (by absorbance at a specific infrared wavelength) against that of water (at another specific infrared wavelength). However, the use of induced pulsations invalidates the use of this device to measure specifically arterial constituents (e.g. oxyhemoglobin) and may well invalidate the measurements of specifically intravascular compounds (e.g. hemoglobin), because the pulsations are likely to cause variations in the light path length through other-than-vascular tissue. This is an especially severe problem when significant amounts of fatty tissue are present. Furthermore, the need to define and produce light at wavelengths that completely or nearly completely separate water from glucose may make the instrument expensive and unwieldy.

In U.S. Pat. No. 5,101,825 to Gravenstein, et al., it is stated that the invention "concerns the simultaneous measurement of volume changes and changes in the mass of either oxyhemoglobin, total hemoglobin, or reduced hemoglobin" in order to quantify the parameter of interest. Gravenstein proposes measuring the pulsatile change in mass of the parameter of interest and dividing that by the pulsatile change in volume of blood flow. One way that Gravenstein suggests to approximate the change in volume of blood flow is to measure the change in length of the light path between the light source and the photo detector. (Example 6). The instant invention, of relating measured changes in absorbance of light at appropriate wavelengths to measured changes in light path length is a much more elegant, accurate and direct way to assess concentrations, because it follows the standard spectrophotometric formula: concentration equals absorbance divided by light path length times extinction coefficient.

Furthermore, Gravenstein asserts that concentration of hemoglobin (or oxyhemoglobin) is proportional to change in mass of these substances divided by change in volume, which is correct only if changing the mass and changing volume can be accurately measured. The pulse oximeter, the only method that Gravenstein specifically discloses to measure mass, measures transmission of light across a digit, sampled by a photodiode of small size relative to the size of the digit. Thus, it cannot sample (and measure) all of the blood present in the digit nor all of the arterial blood pulsing into the digit, and its measurement is proportional to mass only if the pulsatile expansion and contraction of the body part is entirely uniform (and only if the right wavelengths are chosen, etc.). In subjects with varying digit size, the pulse oximeter underestimates, to a varying degree, the actual changing mass of hemoglobin (or oxyhemoglobin). In contrast, volume measurements, by pressure plethysmography, are much less affected by digit size. Thus, ratios of pulse oximeter data to volume change will vary by digit size as well as by hemoglobin concentration.

The availability of a simple, inexpensive, non-invasive monitoring device for measuring various other blood components would greatly simplify diagnosis, would lead to more rapid analysis of blood component concentrations and avoid the risk and discomfort of invasive methods of measuring such components.

A non-invasive blood component analyzer would likely find a substantial market among hospitals, hospital emergency rooms, community emergency medical services, physician's offices, fire and police departments and the like. An accurate, noninvasive glucose analyzer would find an even greater market for the daily, low-cost, home-based self-monitoring of blood glucose by diabetic patients.

SUMMARY OF THE INVENTION

In accordance with the invention, the above and other objects are met by the present non-invasive monitoring device and methods for analysis of blood components.

The invention described here is a noninvasive blood component analyzer using spectrophotometry, with systole/diastole corrections for tissue absorbance, and with built-in monitoring of light path length to allow its accurate use in subjects with widely varying size of finger or other body part.

The present invention for analyzing and monitoring blood component concentrations in a patient is a device that simultaneously measures physical dimensions (e.g., linear distance) and the absorbance of visible and/or infrared light at one or more specific wavelengths across the patient's finger, toe, earlobe, or other body part at each of two or more points in the cardiac cycle, e.g., peak systole and nadir diastole. By these measurements and an analysis of differing absorbances and varying light path lengths, the concentration of a particular blood component can be measured and monitored over time.

Accordingly, it is an object of the present invention to provide a simple, inexpensive, non-invasive monitoring device for blood components.

It is another object of this invention to provide a device and method for simplifying the analysis of the concentration of blood components, including oxyhemoglobin, bilirubin, hemoglobin, glucose, hormones, and a variety of drugs, among others.

Another object of this invention is to provide a device and method for the analysis of blood components that can be used in hospitals, doctors' offices and in patients' homes.

Yet another objective of the present invention is to provide a device and method for analyzing blood components that eases diagnosis and monitors therapy, and if so desired, can be performed by the patient.

Another object of the present invention is to provide a device and method for analyzing blood components that does not require the drawing of blood samples, thereby avoiding discomfort to the patient, the potential for transmission of infectious diseases, and which enhances patient compliance with blood testing.

BRIEF DESCRIPTION OF THE DRAWINGS

Preferred embodiments of the non-invasive blood component analyzer of the present invention are described in detail below with reference to the drawings wherein.

DETAILED DESCRIPTION OF PREFERRED EMBODIMENTS

Figure 2:
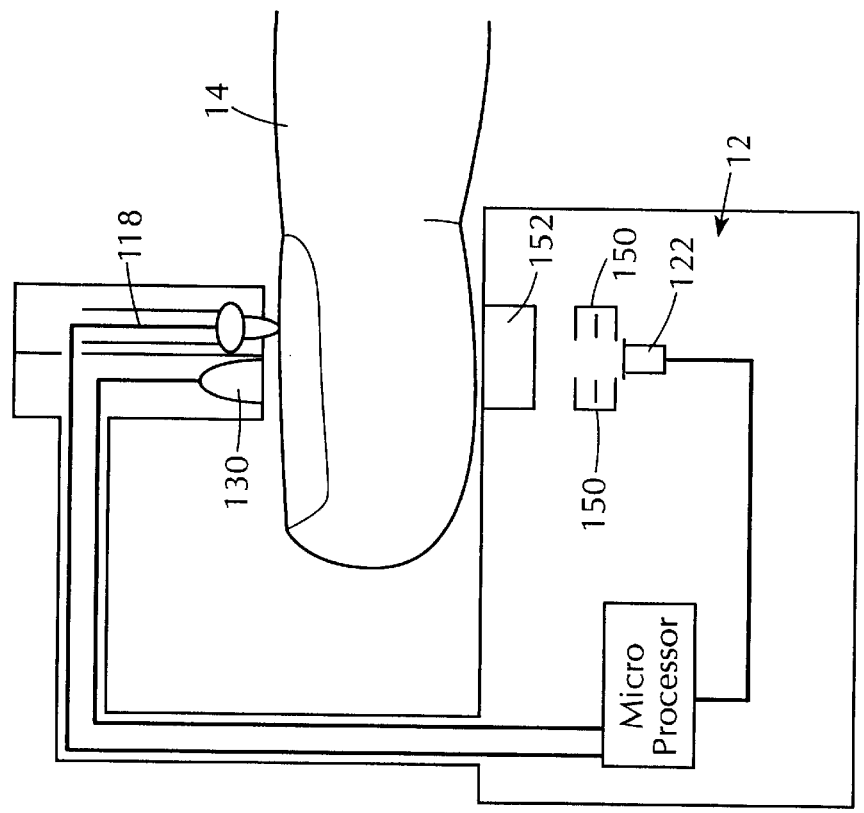
FIG. 2 is a detailed cutaway view of the detector portion of an alternative embodiment of the inventive non-invasive blood component analyzer.

As will become readily apparent to those skilled in the art, although the illustrations in the drawings and the description describe use of a novel non-invasive blood component analyzer, the various features described can be used alone or in combination with other features without departing from the scope of the invention set forth below in the claims.

Figure 1:
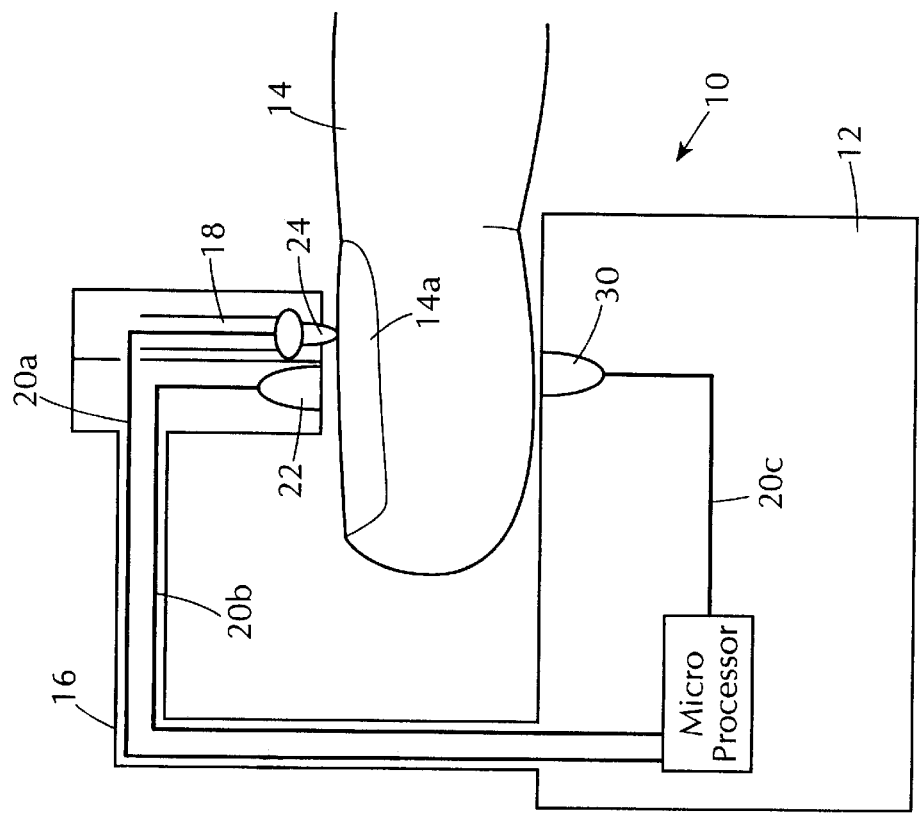
FIG. 1 is a drawing of an embodiment of the inventive non-invasive blood component analyzer.

As shown in FIG. 1, the inventive blood component analyzer 10 is made up of a base 12 which is adapted to accept the patient's finger 14 and holds the finger 14 in place by a means such as a groove, clamp or strap (not shown). The base 12 can be modified to accept and hold (or contour to) a patient's toe or ear or other well-perfused tissue, as will be recognized by one skilled in the art. Firmly embedded in base 12 is arm 16 which is adapted for holding a device for measuring one or more physical characteristics of the tissue, such as a linear displacement transducer 18 (e.g. the miniature displacement transducer made by Solartron Metrology, Buffalo, N.Y.) preferably placed against the patient's fingernail 14a or toenail. The displacement transducer 18 is connected to a microprocessor and display unit (not shown) by lead 20a. The microprocessor and display unit may be embedded in the base 12 or alternatively, the lead 20a can run to an external microprocessor and display unit. The transducer 18 must be adjustable to accommodate digits of varying sizes. This can be accomplished by various mechanical means, which will be recognized by those skilled in the art. The arm 16 is also adapted to hold one or more light-emitting diodes (LEDs), lasers, or other light sources, 22 to produce light at narrow bands of wavelengths in the visible or near-infrared range, depending on the application. The light source 22, preferably should be located as close as possible to the tip 24 of the transducer 18, in order to ensure that both the light source 22 and the transducer 18 are measuring the same tissue path. Further, the arm 16 or light source 22 should be adjustable as discussed above. The intensity of the light source 22 is controlled by the micro processor via a lead 20b. The light source 22 is positioned so as to trans-illuminate the subject's digit 14 or any other body part in which light absorbance of arterial blood can be detected by measuring changes in absorbance during pulsatile flow of blood.. Alternatively, if the light source 22 is too bulky to be conveniently placed next to the subject's digit 14 or other tissue or too hot to be safely placed next to the tissue, it can be positioned at some distance from the tissue on one end of a fiberoptic lightguide, the other end of which is positioned next to the body part 14 alongside the transducer 18.

Light transmitted through the digit 14 is measured by one or more rapidly-responding photodetectors 30. As will be recognized by one skilled in the art, the photodetector 30 and the light source 22 can be alternatively placed in either the base 12 or the arm 16 of the analyzer 10. It is preferred to shield the photodetector 30 from ambient light. The output from the photodetector 30 is transmitted to the microprocessor via lead 20c. The photodetector 30 output is amplified, digitized at 100–500 Hz by an analog-digital converter, analyzed by a microprocessor, and stored as digital files. The microprocessor performs the necessary calculations for this information. A personal computer or some other device for computing can be substituted for the dedicated microprocessor as will be readily recognized by those skilled in the art.

When it is necessary to produce light only in the visible or very near infrared range (approximately 500–1,000 nm), as for measurements of hemoglobin or bilirubin, LEDs are the simplest, most compact, and least expensive option to serve as the light source. Laser diodes are relatively inexpensive and available for a range of wavelengths. Alternatively, an incandescent lamp modified by filters could also be used in the visible range. In the case of near-infrared light, a modified $CO_2$ laser, emitting over a narrow band within the 9,000–10,500 nm range, while expensive, is the simplest option. An alternative is to produce a broad band of infrared emissions using a heater coil, and to narrow the emission band using etalons 152 interposed between the heater coil and the digit (or between the heater coil and one end of a lightguide, the other end of which is positioned next to the digit). Because of the risk of skin or tissue thermal injury from excessive exposure to infrared energy when infrared energy at wavelengths greater than approximately 1,200 nm are used, an electromechanical shutter 152 (e g. Malles-Griot electronic shutter) is interposed between the light source 22 and the digit 14. The shutter is kept closed except for brief (approximately 1/60 sec) periods when photoplethysmographic measurements are required. It will be appreciated by those skilled in the art, both now and as the art progresses, that less risky or costly options can be used.

The linear distance between the light source 22 and the photodetector 30 is monitored with 0.2–0.5 µm resolution by the transducer 18. Alternatively, length is measured by a pair of opposing piezoelectric crystals (e.g. the sonomicrometer made by Triton Technologies, Inc., San Diego, Calif.), sited next to or behind the light source(s) and the photodetector (s). One piezoelectric crystal is electrically excited to generate ultrasonic vibrations and the other piezoelectric crystal measures linear distance between the two by the duration between emission and receipt of the ultrasound signal. A third alternative for measuring length is by a magnetometer, consisting of a pair of coils sited next to the light source(s) and the photodetector(s); one coil generates a magnetic field and the other detects changing magnetic fields and measures linear distance between the two coils by the strength of the detected magnetic field. Similarly, inductance or capacitance proximity or position sensors could be used for the same purpose. Rotary or linear potentiometers could be mechanically linked to both sides of the finger or other body part, to measure linear distance change across the body part. Finally, laser or other optical range finders could be used to measure motion of the fingernail or, if tissue penetrating wavelengths were used, to measure distance across the body part to a target attached to the opposite side.

The result of any of these approaches to measuring the distance between the light source and the base is a "linear plethysmogram" of the fingertip or other body part. The length data are digitized at 100–500 Hz and stored along with the photodetector data. Of course, those skilled in the art will recognize that other physical characteristics, such as circumference of a digit and the changes in circumference, may also be used.

For some applications, e.g., the measurement of hemoglobin, only a single light source 22 emitting at a single wavelength in the visible range will be necessary. In other cases, as for the measurement of glucose, at least two wavelengths both in the near-infrared range, will be required. In such cases, depending on the type of light source used, interposed bandpass filters (e.g. interferometers or etalons supplied by Melles-Griot Photonics Components, Irvine, Calif.) may be used to modify the light produced by the light source.

Turning now to FIG. 2, an alternative embodiment is illustrated for cases in which there is no single wavelength that is strongly absorbed by the compound of interest and by no other compounds expected to be present in arterial blood, such as measuring glucose levels in the subject's blood. In FIG. 2, a single broad-band source 122 is used, and two or more bandpass filters 150 are alternately interposed between the light source and the digit 14 or other tissue, using a rotating or oscillating filter holder 152. Alternatively, two or more separate sources are used, placed adjacent to each other so that the light paths traversed by light from all of the sources to the detector are substantially identical. In this embodiment the two or more light sources are alternately switched on or with their emissions alternately blocked using electromechanical shutters (e.g., Melles-Griot electronic shutter).

When two or more different infrared wavelengths (>1200 nm) are to be investigated, appropriate bandpass filters 150 are sequentially interposed between the digit 114 and the light source 122 for brief periods of time, e.g., 10–20 msec each, by means of a rotating filter holder 152. In another embodiment, two or more light sources are used, alternately switched on for brief periods of time, e.g. 10 msec, or with their emissions alternately blocked by shutters. The photodetector 130 output is monitored during periods of time separately identified as occurring during exposure to each wavelength. For each systole or diastole, average transmittance (T) at each of the relevant wavelengths and average light path length (l) are recorded/computed, and absorbance (A) is calculated as A=log 1/T.

In the embodiment of FIG. 2, where the analyzer 10 is specially adapted to measured substances such as glucose, which requires two or more wavelengths of infrared light, the light source 122 is preferably a heater coil, which in this embodiment is preferably located in base 112. In this case, there is a risk of thermal injury from excessive exposure to heat or infrared energy. In order to reduce exposure of the tissue to IR energy, interposed between the light source 122 and the digit 114 is a electromechanical shutter 152. The shutter 152 is opened for a brief period, e.g. 1/60 second, allowing infrared light to be passed through the digit 114 and detected by the photodetector 130, which in this embodiment is located in the arm 116. Simultaneously, any other operating light source (e.g. an LED producing visible or very near infrared light) is turned off.

Measurements of absorbance of visible or infrared light at one or more specific wavelengths are made across a digit 14, earlobe, or other vascularized tissue at each of two points in the cardiac cycle, near peak systole and near nadir diastole. Simultaneously, the linear distance change due to the influx of arterial blood into the finger 14, or other tissue ($l_{pulse}$) is measured/computed as the difference between distance at the same two points in the cardiac cycle, e.g. peak systole ($l_{syst}$) and nadir diastole ($l_{diast}$).

$$l_{pulse} = l_{syst} - l_{diast}. \quad (1)$$

The absorbance difference at each wavelength $A_{pulse}$ is equal to the systolic-diastolic differences in total tissue absorbance:

$$A_{pulse} = A_{syst} - A_{diast}. \quad (2)$$

Total absorbance of the transilluminating light ($A_{total}$) either at systole or diastole, is the sum of three components: the absorbance by non-blood tissues of the finger ($A_{tissue}$) the absorbance by blood present at diastole (called "venous blood" for convenience) ($A_{ven}$), and absorbance by arterial blood infusing into the finger during systole ($A_{pulse}$):

$$A_{tot} = A_{tissue} + A_{ven} + A_{pulse}. \quad (3)$$

The sum of $A_{tissue}$ and $A_{ven}$ is virtually constant during systole and diastole, so $A_{pulse}$ is the absorbance change due to arterial blood infusing into the finger.

$A_{pulse}$ at any particular wavelength is also equal to the sum of the absorbances due to all of the substances present in the pulsatile arterial blood that absorb at that wavelength: $A_{pulse} = A_x + A_y + A_z + \ldots$ Four configurations of the invention are described, depending upon the strength of the absorption peak used to make the measurement and the presence or absence of interfering substances absorbing at the same wavelength as the substance of interest.

In each of the computations, the results of the calculation may be compared to a reference. References can be derived from a variety of sources, one example of which is a compilation of data from one or more subjects with known or determined levels of blood components.

Example I
Strong Absorption Peak, without Interfering Substances

Figure 3:
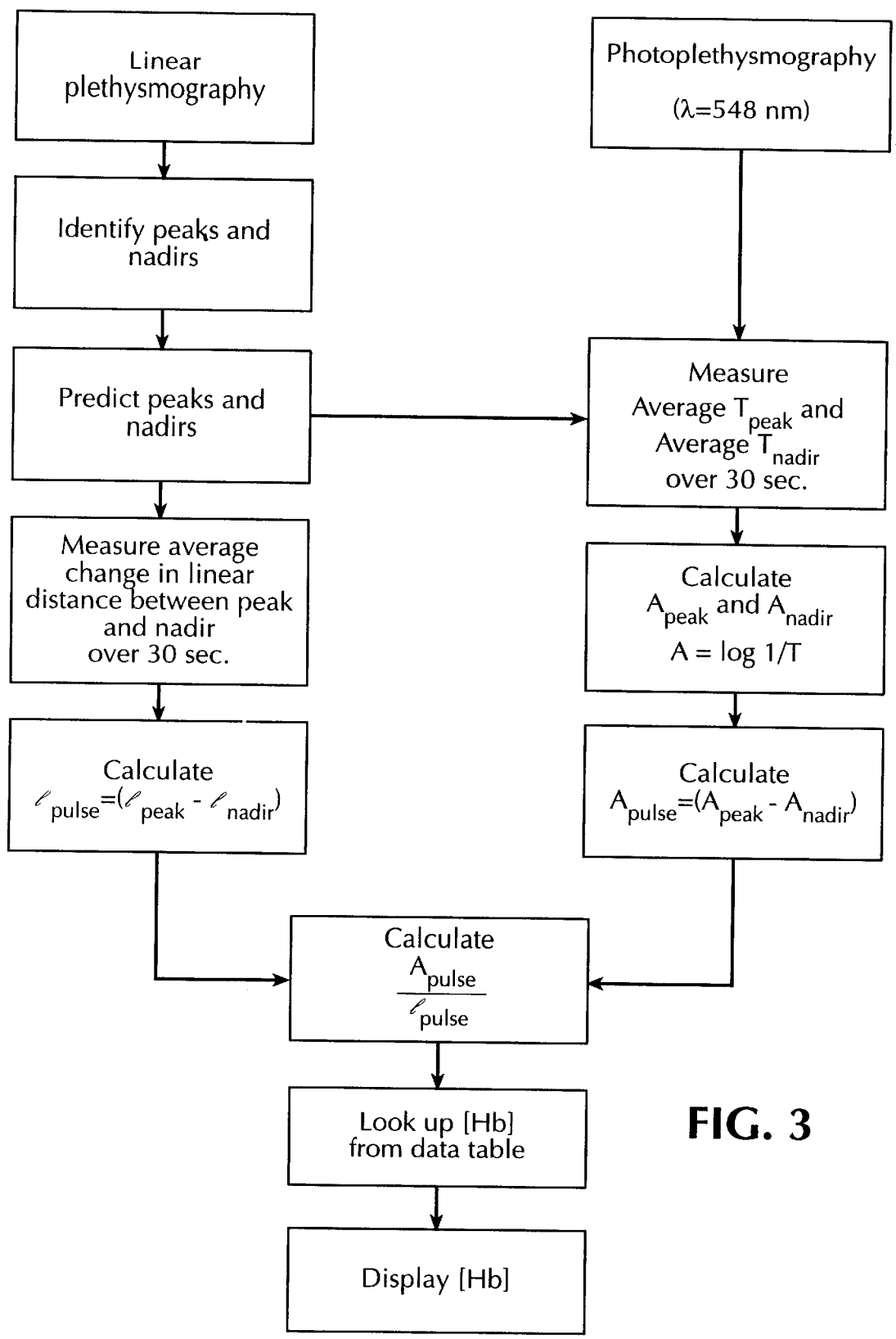
FIG. 3 is a flow chart delineating the steps of a sample method claimed for measuring blood component concentrations when the substance of interest absorbs very strongly at a particular wavelength relative to all other substances expected to be present in blood. (Example I)

As shown in FIG. 3, this configuration is used when the substance of interest absorbs very strongly at a particular wavelength relative to all other substances expected to be present in blood, as, for example, with hemoglobin (Hb) at a wavelength of 548 nm (0.548 μm), an Isosbestic point for oxy-, carboxy-, and reduced hemoglobins. (See, Siek T J, Rieders F., Determination of Carboxyhemoglobin in the Presence of Other Blood Hemoglobin Pigments By Visible Spectrophotometry, *J Forensic Sci* 29:39–54, 1984.) First, two points for analysis are determined, optimally peak systole and nadir diastole. For example, after approximately ten peaks and nadirs of the linear plethysmogram have been identified by the microprocessor, the mean durations between sequential peaks and nadirs are calculated and the times of occurrence of the next peak (systole) and nadir (diastole) are thereby predicted and selected for analysis during subsequent pulses. Since absorbance at 0.548 μm is proportional to hemoglobin concentration and light pulse length, we can say:

$$A_{pulse.548} = [Hb] \cdot \epsilon_{Hb.548} \cdot l_{pulse} \quad (4)$$

where $\epsilon_{Hb.548}$ is the absorptivity of hemoglobin at 548 nm and $l_{pulse}$ is that portion of the light path length that is occupied by pulsatile arterial blood. Rearranging terms, $$[Hb] = A_{pulse.548} / (\epsilon_{Hb.548} \cdot l_{pulse}) \quad (5)$$

To calibrate the instrument, known concentrations of the substance of interest measured from conventional tests on drawn blood from a number of subjects with widely varying test results would be correlated with the ratio of ($A_{pulse.548}/l_{pulse}$), using linear or nonlinear regression analysis, with or without data transformation, as required. Alternatively, if no single regression formula accurately predicts [Hb] from the A/l ratio data over the entire range of A/l values, then separate regressions would be performed over various ranges of A/l data. Subsequently, to use the instrument noninvasively, the derived regression formula or formulae would be used to calculate the concentration of the substance of interest.

Thus, the ratio of systolic-diastolic absorbance divided by the systolic diastolic difference in length can be calibrated to measure hemoglobin concentration, virtually independent of the type and amount of tissue present.

Alternatively, the average rates of change (first derivatives with respect to time) of distance and light absorbance during periods of time that coincide with the steep phases of the linear- and photo-plethysmograms could be used in place of $l_{pulse}$ and $A_{pulse}$.

For practical purposes, since there is no currently available LED emitting at 548 nm, an alternative LED could be used, one emitting at e.g. 586 nm (e.g. the yellow LED made by Hewlett-Packard, part # HSMYR661/R761), a wavelength that is isosbestic for oxy- and reduced hemoglobins, but is absorbed to a much lesser degree by carboxyhemoglobin and met-hemoglobin. It would provide reasonably accurate estimates of total hemoglobin concentrations in all subjects except those rare patients with very high carboxyhemoglobin (or met-hemoglobin) levels, and it would provide accurate estimates of acute changes in hemoglobin (e.g. hemorrhage), even in such patients.

Two other alternative light sources are: (a) a laser diode emitting at 808 nm, close to the 803 nm isosbestic point of oxy- and reduced hemoglobin, or (b) a xenon lamp, modified by high- and low-pass or band-pass filters to narrow the transmitted bandwidth to approximately 800–810 nm (e.g. model 03-FIL-107 or 03-FIL-258 interference filters manufactured by Melles-Griot, Irvine, Calif.). Xenon lamps produce two strong narrow bands of infrared emission with peaks at approximately 820 and 885 nm, along with much lower levels of broad-band visible and infrared light. By filtering out most of the light outside the 800–810 nm range, the result is a relatively inexpensive, relatively monochromatic light source at approximately 810 nm, close to an isosbestic point for oxy- and reduced hemoglobins (803 nm) and a wavelength at which oxy- and reduced hemoglobins absorb similarly.

Another alternative is that the proposed hemoglobin analyzer could be combined with standard, currently available pulse oximetry technology, using two wavelengths, 660 nm and 940 nm. To calibrate the instrument, observed ratios of changing absorbance over changing length (A/l) data at each of the two wavelengths would be correlated against known hemoglobin concentrations in normal subjects, anemic subjects, and polycythemic subjects, using multiple regression analysis, with or without data transformation (logarithmic, exponential, or polynomial). One or more of the best-fit equation would be used as a prediction equation or equations (more than one if the observed data correlate better using different equations over different ranges of observed absorbances or lengths). Such an instrument could be configured to measure oxygen saturation, as well as hemoglobin, allowing arterial oxygen content (hemoglobin concentration (gm/dl) times fractional oxygen saturation times 1.34 ml/gm) to be determined. As with currently available pulse oximeters, the device would overestimate arterial oxygen saturation, and therefore arterial oxygen content, in subjects with high levels of carboxyhemoglobin. For that reason, improved estimates of arterial oxygen content would result if very narrow wavelength bands centered around 548 nm and 578 nm were used; both are isosbestic for carboxy- and reduced hemoglobins, but 548 nm is isosbestic for all three major species of hemoglobin, while 578 nm absorbs oxyhemoglobin more strongly than either carboxy- or reduced hemoglobin. Thus, the 548 nm wavelength would be used to measure total hemoglobin and the comparison of absorbance at 578 nm with that at 548 nm would allow calculation of oxyhemoglobin. Addition of a third wavelength (e.g. 597 nm, isosbestic for oxy- and carboxy-hemoglobins, but absorbing reduced hemoglobin more strongly), would allow separate calculation of reduced and carboxy- in addition to oxy-hemoglobin levels. Similarly, light sources emitting at wavelengths of 506, 521, or 569 nm, all isosbestic for reduced and oxyhemoglobins, could be used in place of the 548 nm emitter.

To simplify instrumentation, virtually any single wavelength in the visible or near-infrared spectrum could be used, along with a linear distance measure and a separate standard pulse oximetric measurement of the saturation of hemoglobin with oxygen ($O_2$sat), which would be obtained simultaneously using standard pulse oximeter technology, but not necessarily from the same finger or other body part. The instrument would be calibrated by multiple regression of A/l and $O_2$sat (measured by standard pulse oximeter) against measured hemoglobin in normal subjects, subjects with anemia, and subjects with polycythemia, and in subsequent noninvasive clinical use, hemoglobin would be calculated from the regression coefficients applied to two variables: the A/l ratio and the $O_2$sat.

A further alternative is that supplemental oxygen could be administered to subjects undergoing noninvasive hemoglobin analysis, to, for practical purposes, eliminate reduced hemoglobin from arterial blood. Sufficient oxygen would be administered by nasal cannula or facemask to bring a standard pulse oximeter reading to 99–100% (usually 2–5 minutes of 2–5 lpm flow via nasal cannula). The proposed hemoglobin analyzer would then measure changing absorbance to changing length ratios at virtually any wavelength in the visible or near-infrared spectrum.

650 nm would be one possible choice, convenient because LEDs emitting at that wavelength are commercially available and because oxy- and carboxyhemoglobins are isosbestic at that wavelength, so that, in the absence of reduced hemoglobin, the absorbance to length ratio would correlate with total hemoglobin. Met-hemoglobin would cause overestimation of total hemoglobin concentration because met-hemoglobin absorbs much more strongly at 650 nm than do either oxy- or carboxyhemoglobin, but methemoglobinemia is rare and can be discounted in most cases.

940 nm would be another possible choice, convenient because LEDs emitting at that wavelength are commercially available and because carboxyhemoglobin has virtually absent absorbance at that wavelength, so that, in the absence of reduced hemoglobin, the absorbance/length ratio would correlate with "effective" hemoglobin, the hemoglobin that is available for oxygen transport. Again, met-hemoglobin would cause overestimation of total hemoglobin concentration.

Those skilled in the art will recognize that many different sets of wavelengths would be suitable—if two wavelengths are used, oxy- and reduced hemoglobins could be discriminated; if three wavelengths are used, oxy-, carboxy-, and reduced hemoglobins could be discriminated; if four wavelengths are used, oxy-, carboxy-, met-, and reduced hemoglobins could be discriminated; and if five wavelengths are used, oxy-, carboxy-, met-, sulf-, and reduced hemoglobins could be discriminated.

Example II
Weak Absorption Peak, without Interfering Substances

Figure 4:
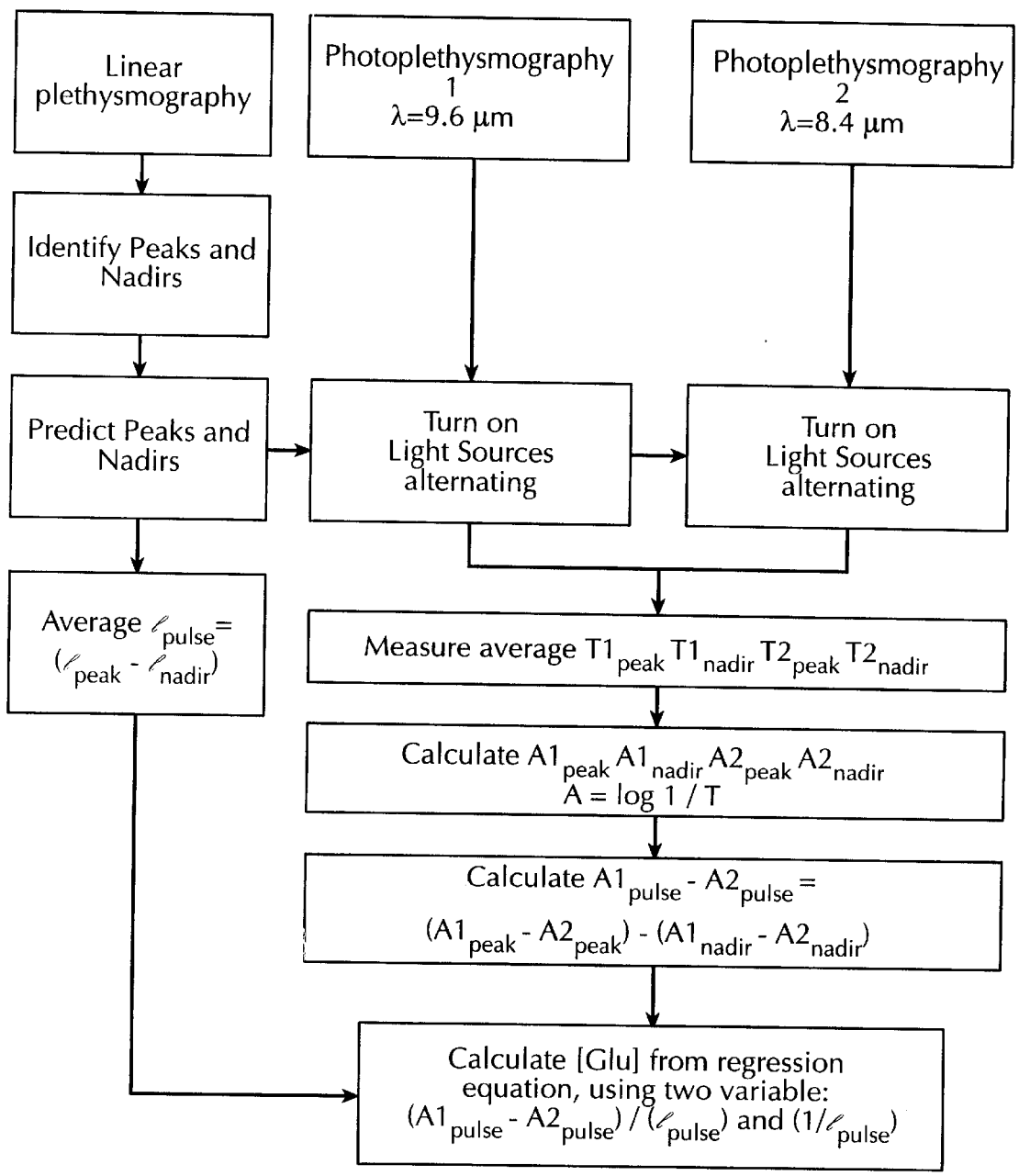
FIG. 4 is a flow chart delineating the steps of a sample method claimed for measuring blood component concentrations when there is only a weak absorption peak for the substance of interest, i.e., in the case of the measurement of glucose concentration. (Example II)

This configuration would be used when only a weak absorption peak at a particular wavelength $\lambda_1$ exists for the substance of interest. In such cases, a second (reference) wavelength ($\lambda_2$) with relatively low absorption by the substance of interest and by all other substances expected to be present in blood would also be studied. An example is glucose, which has a relatively weak absorption peak at 9.6 $\mu$m (9600 nm), but one that is specific to glucose, as compared to hemoglobin and plasma proteins. Zeller H, Novak P, Landgraf R., Blood Glucose Measurement by Infrared Spectroscopy, *Intl J Artif Org* 12:12–35, 1989. The difference between absorbance at 9.6 $\mu$m and absorbance at a reference wavelength of 8.4 $\mu$m (8400 nm) would allow relatively good separation of glucose from plasma proteins and hemoglobin. The calculation is set forth in FIG. 4. In this case, since the total absorbance difference between the two wavelengths will be relatively independent of the concentration of substances other than glucose, $$A_{pulse\ 9.6} - A_{pulse\ 8.4} = (([glu] \cdot l_{pulse}) \cdot (\epsilon_{glu9.6} - \epsilon_{glu8.4})) + k. \qquad (6)$$

(where $\epsilon_{glu9.6}$ and $\epsilon_{glu8.4}$ are absorptivities of glucose at 9.6 and 8.4 $\mu$m, respectively, and k is a small and, for practical purposes, constant term due to differences in absorbance of water and other blood components between 9.6 and 8.4 $\mu$m). Rearranging terms, $$[glu] = (A_{pulse\ 9.6} - A_{pulse\ 8.4} - k)/(l_{pulse} \cdot (\epsilon_{glu9.6} - \epsilon_{glu8.4})). \qquad (7)$$

If we express $A_{pulse\ 9.6-8.4} = A_{pulse\ 9.6} - A_{pulse\ 8.4}, k_1 = 1/(\epsilon_{glu9.6} - \epsilon_{glu8.4})$, and $k_2 = k/(\epsilon_{glu9.6} - \epsilon_{glu8.4})$, then $$[glu] = (k_1 \cdot A_{pulse9.6-8.4}/l_{pulse}) - (k_2/l_{pulse}). \qquad (8)$$

The absorbances are calculated from measured transmittances, $l_{pulse}$ is measured, and $k_1$ and $k_2$ are constants that can be empirically determined by comparison with standard measurements.

To calibrate the instrument, known concentrations of the substance of interest measured from conventional tests on drawn blood would be correlated with two variables: ($A_{pulse9.6-8.4}/l_{pulse}$) and ($1/l_{pulse}$), using multiple regression analysis, with or without data transformation, as required. Alternatively, if no single regression formula accurately predicts [Glu] over the entire range of absorbance and length values, then separate regressions would be performed over various ranges of $1/l$ or absorbance data. Subsequently, to use the instrument noninvasively, the derived regression formula or formulae would be used to calculate the concentration of the substance of interest.

Optimally, the light sources would be switched on and off quickly enough so that the absorbance measurements at systole and diastole occur at essentially the same times for both wavelengths. Alternatively, if the unavoidable differences in timing of absorbance measurements result in significant errors in prediction of the concentration of the substance of interest, then light path length data would be separately collected at the appropriate times to be related to each wavelength (e.g. $l_{pulse\ 9.6}$ and $l_{pulse\ 8.4}$) and the regression analysis would be carried out using three variables:

$$(A_{pulse\ 9.6}/l_{pulse\ 9.6})-(A_{pulse\ 8.4}/l_{pulse\ 8.4}),\ 1/l_{pulse\ 9.6},\ \text{and}\ 1/l_{pulse\ 8.4}$$

EXAMPLE III
Interfering Substances Present

Figure 5:
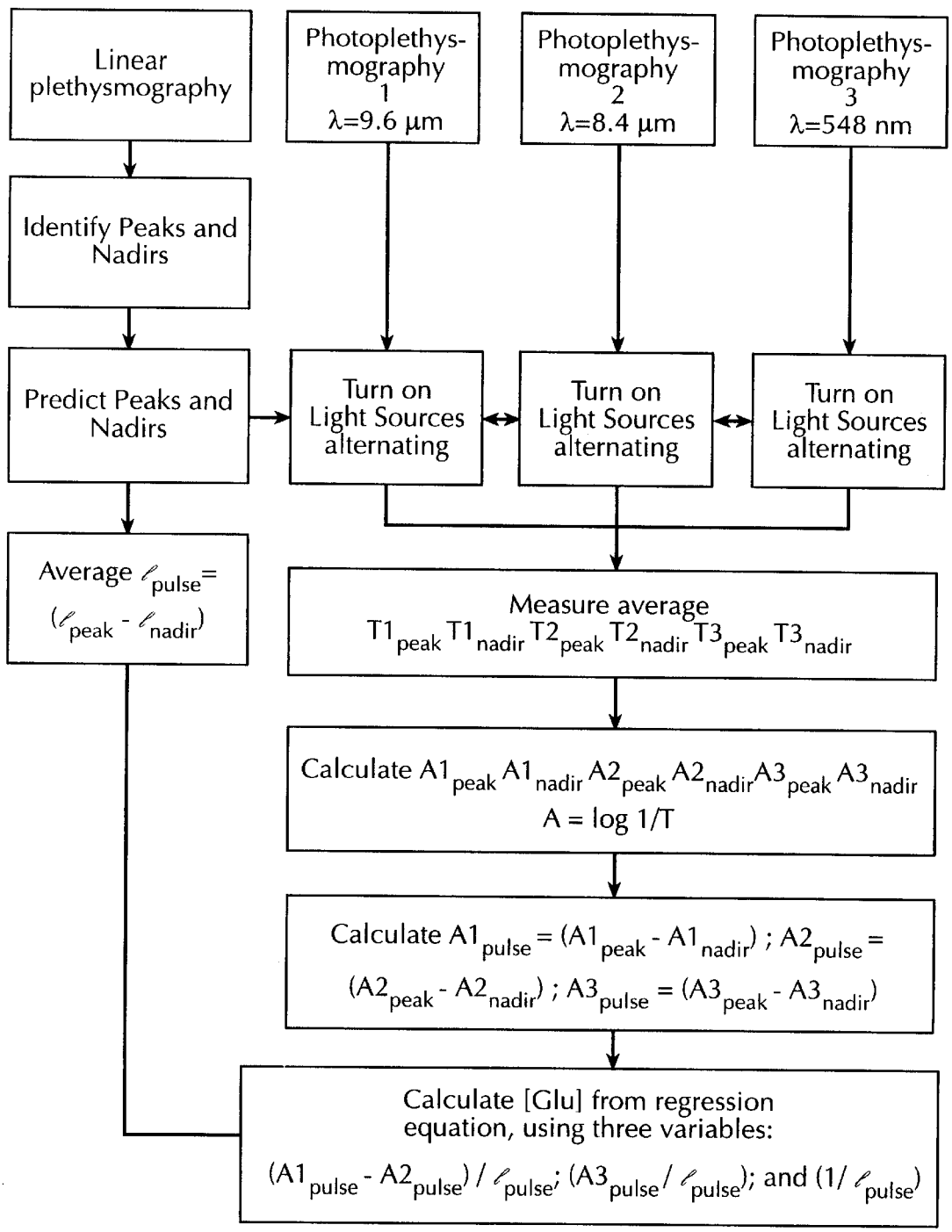
FIG. 5 is a flow chart delineating the steps of a sample method claimed for measuring blood component concentrations when a single interfering substance is present at the optimal wavelength. (Example III)
Figure 6:
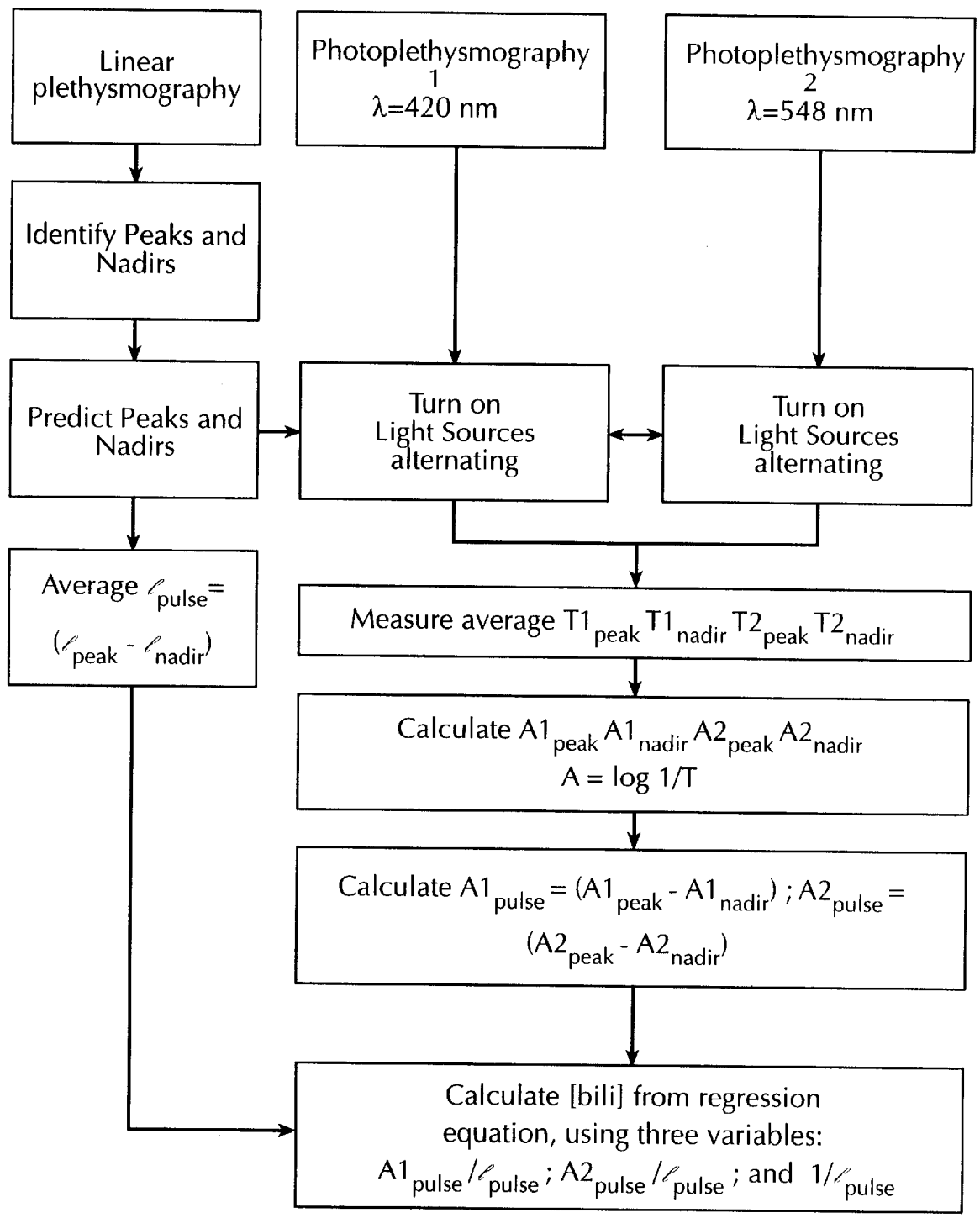
FIG. 6 is a flow chart delineating the steps of a sample method claimed for measuring blood component concentrations when a single interfering substance is present at the optimal wavelength, but no reference wavelength is needed, such as in the case of the measurement of bilirubin concentration. (Example IV)

When a single interfering substance is present at the optimal wavelength to detect a substance, a third wavelength is used to correct for the presence of the interfering substance. An example is glucose and hemoglobin at a wavelength of 9.02 μm, a stronger peak for glucose than is 9.6 μm but one at which hemoglobin also absorbs. This calculation is shown in FIG. 5.

$$A_{pulse\ 9.02}-A_{pulse\ 8.4}=\{([glu]\cdot l_{pulse})\cdot(\epsilon_{glu-9.02}-\epsilon_{glu-8.4})\}+\{([Hb]\cdot l_{pulse})\cdot(\epsilon_{Hb9.02}-\epsilon_{Hb8.4})\}+k \quad (9)$$

But, as noted above, $[Hb]=A_{pulse.548}/(\epsilon_{Hb.548}\cdot l_{pulse})$. Substituting for [Hb]:

$$A_{pulse\ 9.02}-A_{pulse\ 8.4}=\{([glu]\cdot l_{pulse})\cdot(\epsilon_{glu9.02}-\epsilon_{glu8.4})\}+\{(A_{pulse.548}/\epsilon_{Hb.548})\cdot(\epsilon_{Hb9.02}-\epsilon_{Hb8.4})\}+k \quad (10)$$

Rearranging terms, $$[glu]=A_{pulse\ 9.02}-A_{pulse\ 8.4}-k-\{(A_{pulse.548}/\epsilon_{Hb.548})\cdot(\epsilon_{Hb9.02}-\epsilon_{Hb8.4})\}/\{(l_{pulse}\cdot(\epsilon_{glu9.02}-\epsilon_{glu8.4})\} \quad (11)$$

All of the absorptivities are constants. If we express $A_{pulse\ 9.02-8.4}=(A_{pulse\ 9.02}-A_{pulse\ 8.4})$, $k_1=1/(\epsilon_{9.02}-\epsilon_{glu\ 8.4})$, $k_2=(\epsilon_{Hb9.02}-\epsilon_{Hb8.4})/\{\epsilon_{Hb.548}\cdot(\epsilon_{glu9.02}-\epsilon_{glu8.4})\}$, and $k_3=k/(\epsilon_{glu9.02}-\epsilon_{glu8.4})$, then $$[Glu]=(k_1\cdot A_{pulse9.02-8.4}/l_{pulse})-(k_2\cdot A_{pulse548}/l_{pulse})-(k_3/l_{pulse}) \quad (12)$$

To calibrate the instrument, known concentrations of the substance of interest measured from conventional tests on drawn blood would be correlated with three variables: ($A_{pulse9.02-8.4}/l_{pulse}$), ($A_{pulse.548}/l_{pulse}$) and ($1/l_{pulse}$), using multiple regression analysis, with or without data transformation, as required. Alternatively, if no single regression formula accurately predicts [Glu] over the entire range of absorbance or length values, then separate regressions would be performed over various ranges of absorbance or length data. Subsequently, to use the instrument noninvasively, the derived regression formula or formulae would be used to calculate the concentration of the substance of interest.

Thus, for this configuration, physical measurements such as linear distance changes and absorbance changes at each of three different wavelengths, in this example, 0.548, 8.4, and 9.02 μm, would have to be studied. Those skilled in the art will recognize that many other sets of wavelengths could be used. Furthermore, the use of first derivative spectroscopy would improve the accuracy of the technique.

As in example II, it might be necessary to measure $l_{pulse}$ separately for each of the three wavelengths, making the calculations slightly more complex, as outlined above.

EXAMPLE IV
Interfering Substance at Strong Absorption Peak

Another example of a substance that could be measured after correction for the presence of an interfering substance is bilirubin. Bilirubin has a strong absorption peak around 420 nm, but hemoglobin absorbs substantially at that wavelength. As described above, bilirubin could be measured using two wavelengths: approximately 420 nm to detect bilirubin (without the need for a reference wavelength) and 548 nm (or 506, 521, 569, or 586 nm as discussed above) to correct for the presence of hemoglobin.

$$A_{pulse.42}=([bili]\cdot l_{pulse}\cdot\epsilon_{b.42})+([Hb]\cdot l_{pulse}\cdot\epsilon_{Hb.42})+k. \quad (13)$$

But, as noted above, $[Hb]=A_{pulse.548}/(l_{pulse}\cdot\epsilon_{Hb.548})$. Substituting for [Hb], $$A_{pulse.42}=([bili]\cdot l_{pulse}\cdot\epsilon_{b.42})+(A_{pulse.548}\cdot\epsilon_{Hb.42}/\epsilon_{Hb.548})+k. \quad (14)$$

Rearranging terms, $$[bili]=\{A_{pulse.42}-(A_{pulse.548}\cdot\epsilon_{Hb.42}/\epsilon_{Hb.548})-k\}/l_{pulse}\cdot\epsilon_{b.42}). \quad (15)$$

If we express $k_1=1/\epsilon_{b.42}$, $k_2=\epsilon_{Hb.42}/(\epsilon_{Hb.548}\cdot\epsilon_{b.42})$, and $k_3=k/\epsilon_{b.42}$, then $$[bili]=(k_1\cdot A_{pulse.42}/l_{pulse})-(k_2\cdot A_{pulse.548}/l_{pulse})-(k_3/l_{pulse}). \quad (16)$$

To calibrate the instrument, known concentrations of the substance of interest measured from conventional tests on drawn blood would be correlated with three variables: $A_{pulse.42}/l_{pulse}$, $A_{pulse.548}/l_{pulse}$, and $1/l_{pulse}$, using multiple regression analysis, with or without data transformation, as required. Alternatively, if no single regression formula accurately predicts the substance of interest over the entire range of absorbance and length values, then separate regressions would be performed over various ranges of $1/l$ or absorbance data. Subsequently, to use the instrument noninvasively, the derived regression formula or formulae would be used to calculate the concentration of the substance of interest.

Because of the strong absorbance by oxyhemoglobin at 420 nm, 475 nm might be a better choice. At 475 nm, a wavelength at which LEDs are commercially available, bilirubin absorbs relatively strongly (though not at its peak), while hemoglobin (both oxy- and reduced) absorbs relatively poorly. Despite the relatively low absorbance by hemoglobin, the much higher concentration of hemoglobin than of bilirubin in arterial blood makes it necessary to correct for the presence of hemoglobin, using a comparison wavelength, e.g. 548, 586, or 803 nm, which are isosbestic for oxy- and reduced hemoglobins, as discussed above.

A further alternative is to use three wavelengths, e.g. 475, 660, and 940 nm, along with a linear distance measurement, to measure three unknowns, bilirubin, oxyhemoglobin, and reduced hemoglobin. Analogous to the discussion of the hemoglobin measurements above, it would also be possible to use a separate pulse oximetric measurement of $O_2$sat and only two wavelengths (e.g. 475 and 940 nm) rather than three wavelengths to correct for hemoglobin in the measurement of bilirubin. Bilirubin would be calculated from three variables: the A/l ratios at 475 and 940 nm and the $O_2$sat.

Yet another alternative would be to provide supplemental oxygen to subjects undergoing noninvasive bilirubin hemoglobin analysis, to, for practical purposes, eliminate reduced hemoglobin from arterial blood and to allow virtually any wavelength between approximately 530 and 1000 nm to serve as a correction for hemoglobin.

Again, as in examples II and III, it might be necessary to measure $l_{pulse}$ separately for each of the wavelengths.

For each of the above configurations, the concentration of the appropriate blood component is calculated from one of the regression equations derived as described above. Data are averaged over the period of time required to generate reliable-average data, e.g. over every thirty to sixty seconds, or every 50 to 100 pulses.

FURTHER EXAMPLES

A pulse oximeter manufactured by Medical Research Laboratories, Inc. (MRL, Buffalo Grove, Ill.) was modified so that the brightness of the red (660 nm) and infrared (940 nm) LEDs could be externally adjusted by application of a known voltage to the LED control circuit. The points at which the DC and AC components of the red and infrared photoplethysmograms could be separately sampled were identified from the pulse oximeter's circuit diagram. Voltage was sampled at those points and digitized by a 16 bit A-D converter interfaced with a personal computer. The LED and photodiode assemblies were dissected out of an MRL fingertip probe to allow them to move freely with pulsatile expansion and contraction of tissue across which they are placed.

Two methods were used to collect linear photoplethysmographic data:

For the first method, the palmar surface of a finger was rested on a hard surface with the photodiode assembly from the MRL pulse oximeter placed between the finger and the hard surface. A Solartron Metrology linear displacement transducer (1.5 mm range) was placed up against the LED assembly, perpendicular to the fingernail, so as to measure the changes in fingertip diameter along the approximate light path traversed between the LEDs and the photodiode. The linear displacement transducer was excited at 5000 Hz and its output converted to voltage and amplified by a Solartron Metrology signal conditioner. Data from the linear displacement transducer, DC and AC data from both the infrared and red photoplethysmograms from the pulse oximeter, and the voltage controlling the brightness of the pulse oximeter LEDs were sampled continuously at 150 Hz and stored as digital files in the PC for later analysis.

Figure 7:
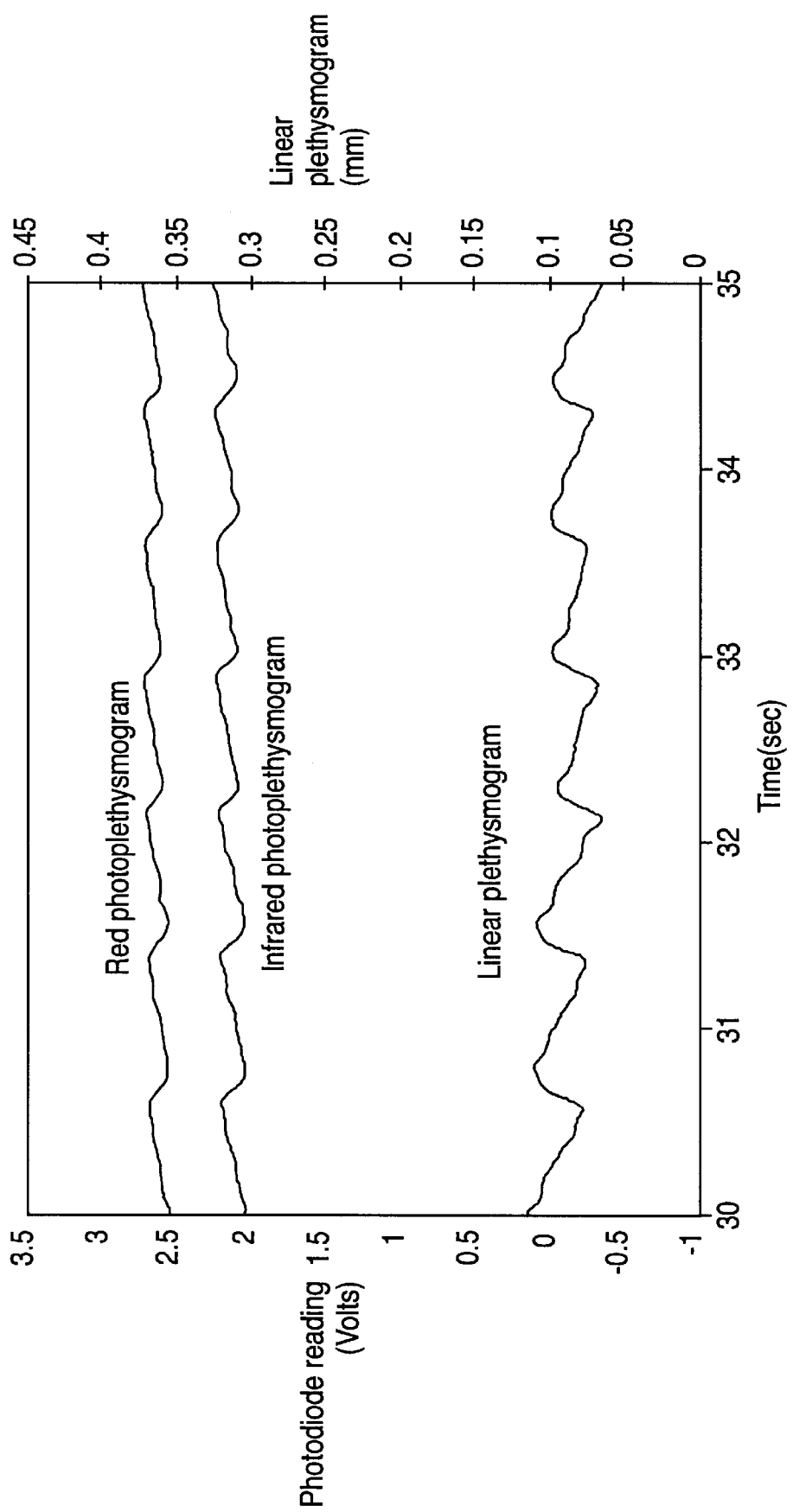
FIG. 7 is exemplary raw photoplethysmographic and linear plethysmographic data.

Preliminary experiments have demonstrated that stable photoplethysmographic and linear plethysmographic data can be obtained from cooperative subjects using this technique (see FIG. 7). FIG. 7 is exemplary raw photoplethysmographic and linear plethysmographic data obtained from the index finger of one normal subject, using a modified MRL pulse oximeter and a Solartron Metrology linear displacement transducer. However, the linear plethysmogram was variably damped in the individual subjects studied at different sittings, probably because of variations in muscle tone. This variable damping yielded widely varying ratios of pulsatile changes in absorbance to pulsatile changes in length. Linear displacement transducer may serve as an acceptable method to measure changes in light path length if these variables can be controlled.

For the second method to evaluate the linear plethysmogram, 1 mm sonomicrometer transducers (model SA 5-1, Triton Technology, San Diego, Calif.) were glued onto the LED and photodiode assemblies from the MRL fingertip probe immediately adjacent to the LEDs and the photodiode. After the skin was cleansed with alcohol and painted with tincture of benzoin (to enhance skin adhesiveness), the LED and photodiode assemblies were secured on either side of a fingertip or earlobe using adhesive tape. One of the sonomicrometer transducers served as the "pinger" generating ultrasonic vibrations while the other served as the receiver. The sonomicrometer signals were conditioned by a Triton Technology model 150 sonomicrometer module, yielding analog signals proportional to the linear distance between the two transducers. The analog output was digitized at 150 Hz, along with DC and AC data from both the infrared and red photoplethysmograms from the pulse oximeter, and the voltage controlling the brightness of the pulse oximeter LEDs, and stored as digital files in the PC for later analysis.

Figure 10:
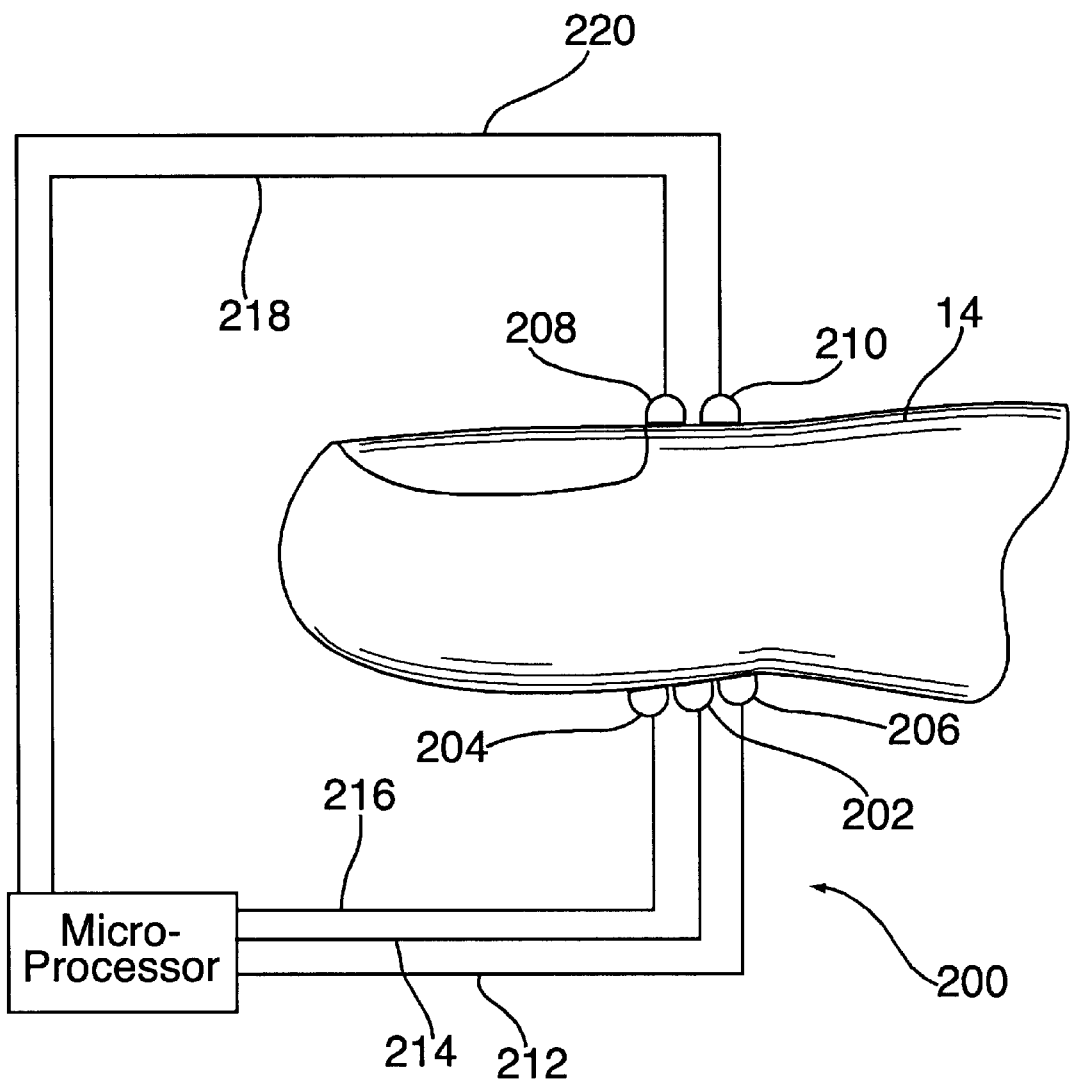
FIG. 10 is a schematic drawing of an alternative embodiment of the inventive non-invasive blood component analyzer.

FIG. 10 is a schematic diagram of instrument 200 to measure hemoglobin or other blood component noninvasively, using two wavelengths of light generated by LEDs and sonomicrometers to measure changing light path length. A sonomicrometer transducer 202 and one (or two) light-emitting diodes (LEDs) 204, 206 are applied to one side of a body part, e.g. fingertip 14, by means of adhesive tape, cyanoacrylate, or other adhesive agent. Directly on the opposite side of the body part, another sonomicrometer transducer 208 and a photodiode 210 are similarly applied. Highly flexible wire leads 212–220 connect the sonomicrometer transducers, the LEDs, and the photodiode to a microprocessor 222 which includes signal conditioners.

The data were displayed on a spreadsheet, and, after removal of high-frequency artifacts from the sonomicrometer signals, the onset of each arterial pulse was identified as a peak of light transmission simultaneous with a valley of linear distance. The change in light absorbance at each wavelength over the subsequent pulse was measured as the logarithm of the reciprocal of the relative change in light transmission. The change in linear distance over the same period was measured as the change in the sonomicrometer signal, multiplied by a calibration factor (mm per Volt), determined in vitro. The changing absorbance to changing length ratio (A/l for each wavelength was then averaged over the 5 to 10 data points (33 to 67 msec) near the subsequent valley of light transmission (and peak of linear distance), yielding an average A/l for that pulse at that wavelength. Calculated A/l values for each pulse were averaged over at least 20 pulses at each wavelength.

Figure 8:
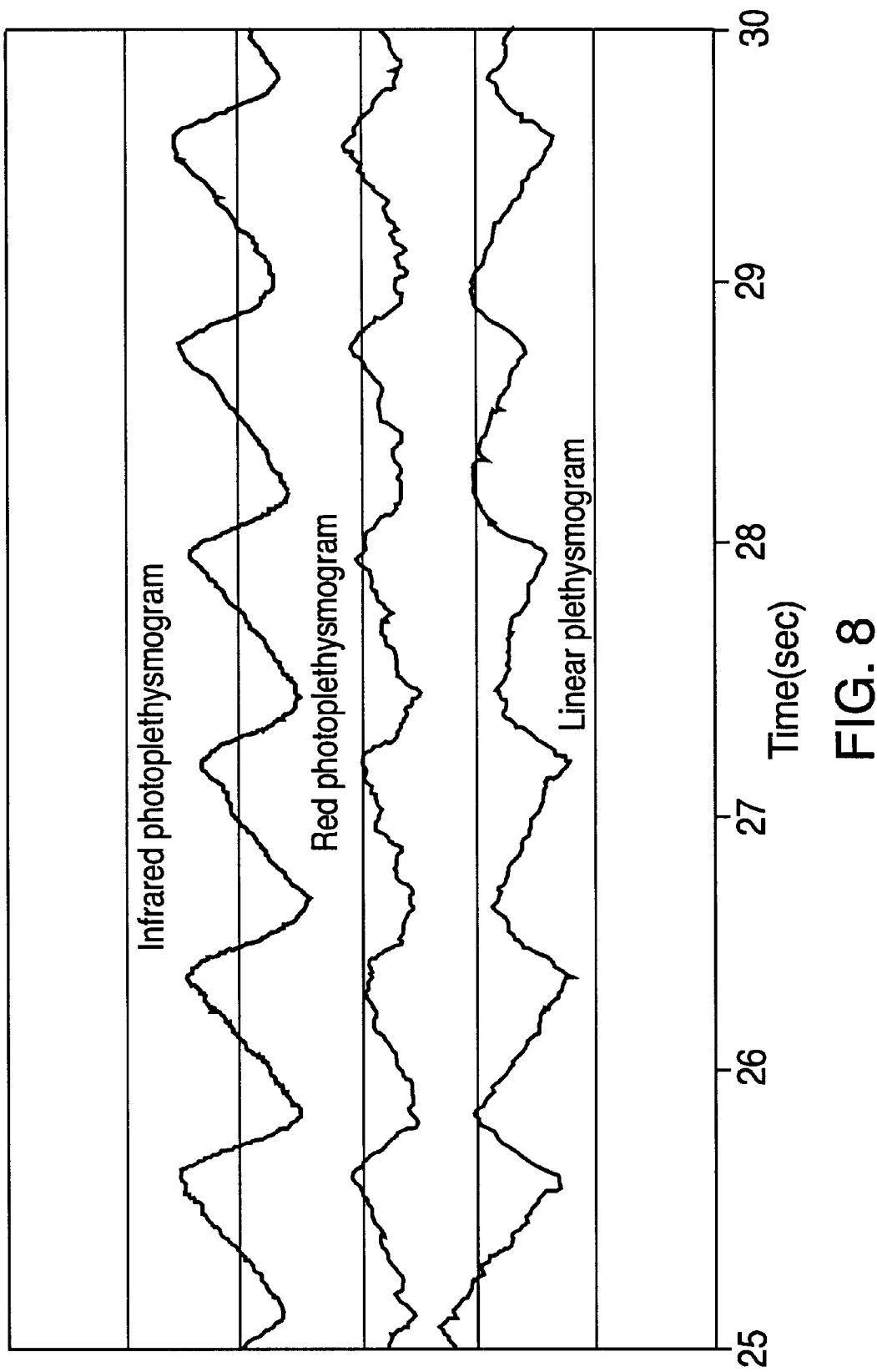
FIG. 8 is exemplary raw photoplethysmographic and linear plethysmographic data.
Figure 9:
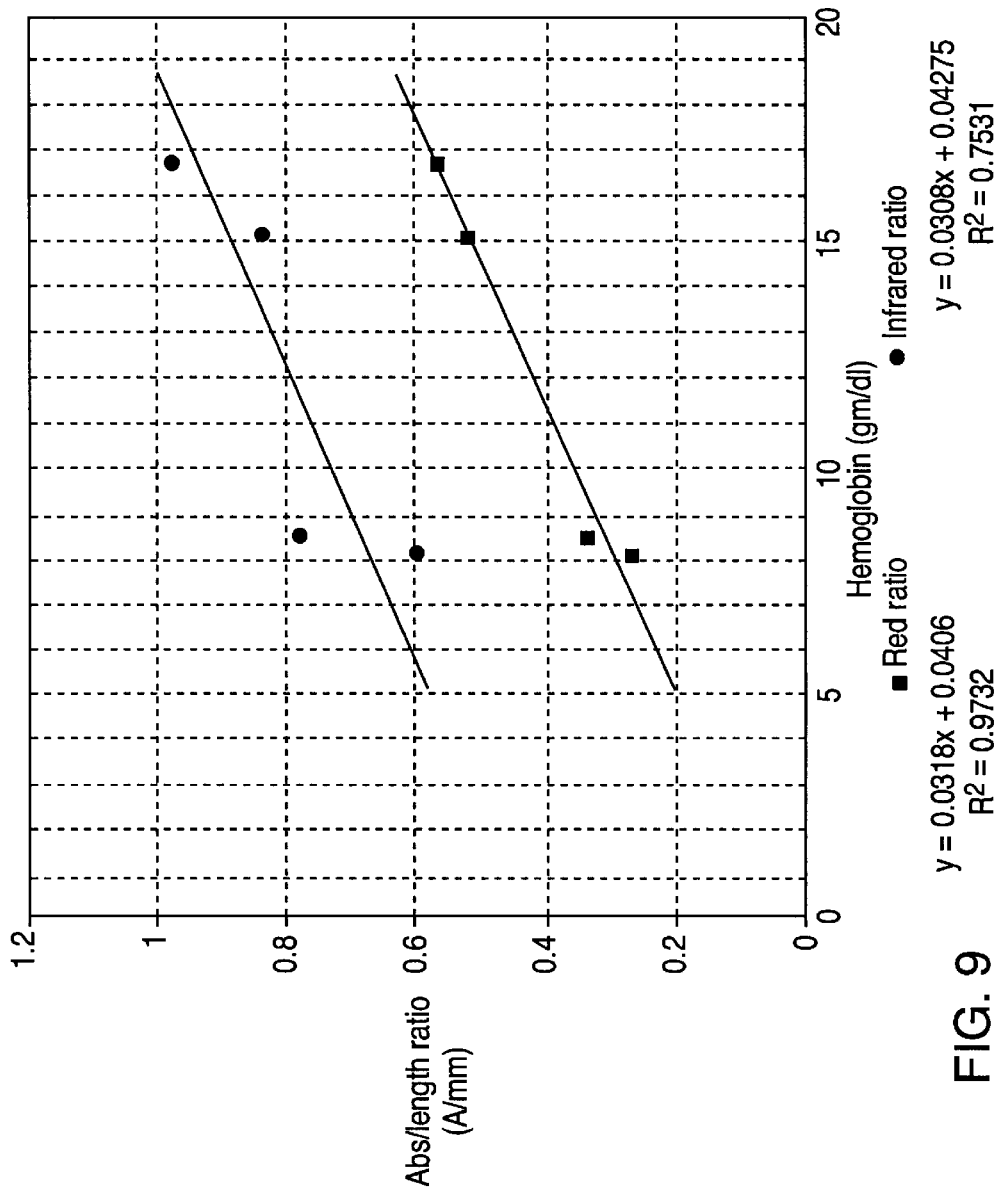
FIG. 9 is a chart showing average changing absorbance to changing length ratios at red (660 nm) and infrared (940 nm) wavelengths plotted against blood hemoglobin for exemplary subjects.

With this technique, stable photoplethysmographic and linear plethysmographic data could be obtained from the fingertip of most subjects and from the earlobe of the normal subjects. FIG. 8 is exemplary raw photoplethysmographic and linear plethysmographic data obtained from the fifth finger of one normal subject, using a modified MRL pulse oximeter and a Triton Technology sonomicrometer. Preliminary data from four naive subjects with known blood hemoglobin (and carboxy- and met-hemoglobin) levels breathing supplemental oxygen sufficient to bring their oxygen saturations to 99–100% (in order to ensure that, for practical purposes, no reduced hemoglobin was present in arterial blood) demonstrate a strong linear correlation between hemoglobin and the ratios of changing red or infrared absorbance to changing linear distance. FIG. 9 is a chart showing average changing absorbance to changing length ratios at red (660 nm) and infrared (940 nm) wavelengths plotted against blood hemoglobin for exemplary subjects (measured in drawn blood by standard techniques) for each of four subjects with $O_2$sat 99–100%: two anemic, one normal, and one slightly polycythemic. These preliminary data show highly significant correlations between absorbance/length ratios at each wavelength and gold-standard hemoglobin measurements. Additional data collection could be used to refine the regression analysis and to generate a prediction equation or equations allowing total hemoglobin to be predicted from A/l data either from the 660 nm data, the 940 nm data, or both.

Figure 11:
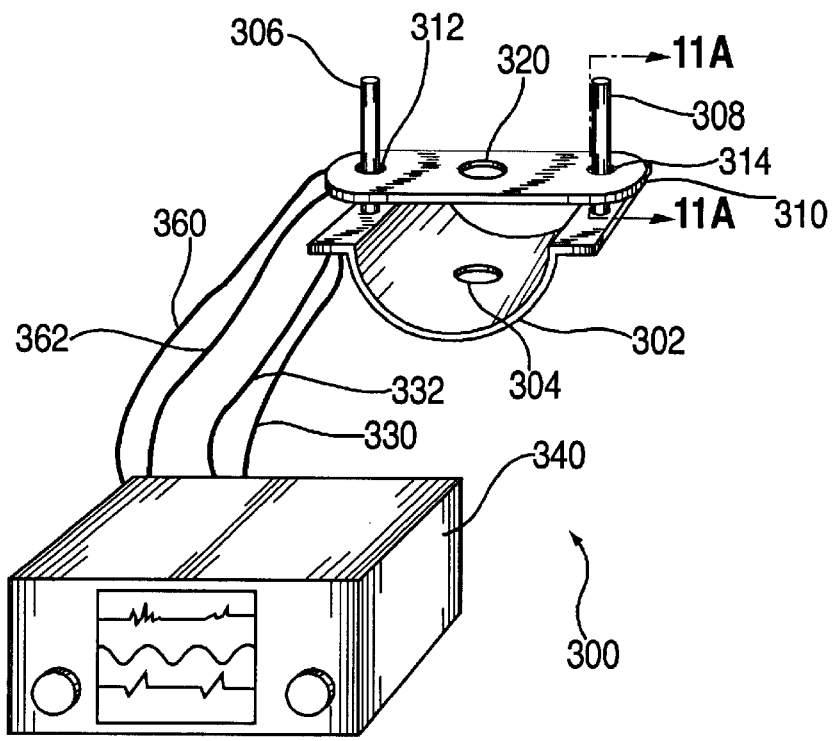
FIG. 11 is a schematic drawing of yet another alternative embodiment of the inventive non-invasive blood component analyzer.
Figure 11A:
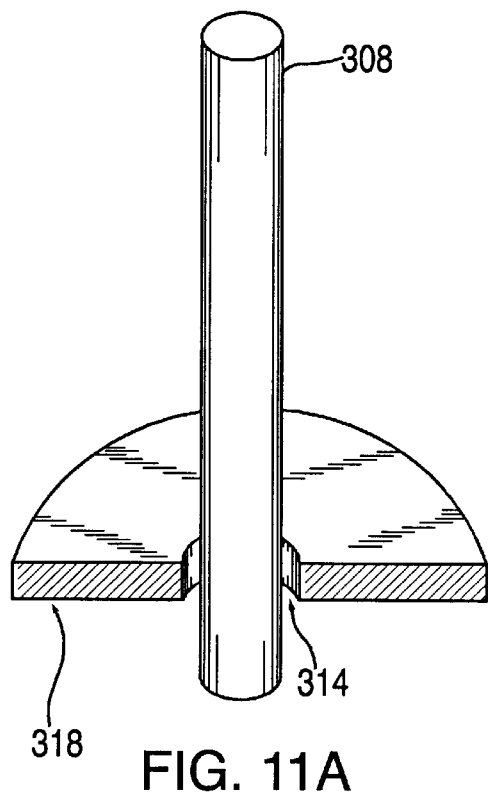
FIG. 11A is a cutaway view of one component of the device of FIG. 11.

FIG. 11 is a schematic diagram of another embodiment of an instrument to measure hemoglobin or other blood component noninvasively, measuring changing absorbance of one or more wavelengths of light generated by LEDs and measuring changing light path length with modified linear displacement transducers. FIG. 11A is a cutaway view of one component of the device of FIG. 11. A fingertip or other body part (not shown) is rested in a rigid base 302 contoured to hold the body part against an incorporated photodiode or other light-sensing device 304. Rigid posts 306, 308, in which are contained coils from linear displacement transducers, rise perpendicularly from the base in the same plane as the light sensing-device. A light-weight slider 310 is placed over the two posts 306–308 and rests on top of the finger or other body part (not shown). Two holes 312, 314 allow the slider 310 to slide up and down vertically over the posts 306, 308. Incorporated in the slider 310 are two coils 316, 318 (FIG. 11A) located circumferentially around the holes 312, 314, making the posts 306, 308 and their incorporated coils 316, 318 function as linear displacement transducers. Also incorporated into the slider 310 directly opposite and facing the light sensor 304 are one or more LEDs or other light-emitting devices 320. Wire leads 330, 332 connect the light sensor 304 and the coils 316, 318 incorporated into the posts 306, 308 to signal conditioners, a microprocessor, and display 340. Highly flexible wire leads 360, 362 connect the light source(s) 320 and the coils 316, 318 incorporated into the slider 310 around the hole 312, 314 to the signal conditioners, microprocessor, and display 340. It will be recognized by those skilled in the art that positions of the light source(s) and light sensor could be reversed. It will also be recognized that alternative methods of sensing motion of the slider 310 could be used, e.g. laser range finders or capacitive or inductive proximity sensors mounted on the base 302 or in a separate housing where they can detect motion of the slider 310 relative to the base 302. It will further be recognized that the slider 310 need not be straight, but could be angled, and that it could actually be attached to the base, with its motion relative to the base sensed by linear or rotary potentiometers.

Although an exemplary embodiment of the invention has been described in detail above, those skilled in the art will readily appreciate that many additional modifications are possible in the exemplary embodiment without materially departing from the novel teachings and advantages of the invention. Accordingly, all such modifications are intended to be included within the scope of the invention as defined in the following claims.

What is claimed is:

1. A non-invasive method for measuring the concentration of a blood component in a subject's blood, said method comprising the steps of:

a. providing at least one light source for directing light of at least two wavelengths through a tissue of the subject in which light absorbances by arterial blood can be detected by measuring changes in absorbance during pulsatile flow of blood;

b. providing at least one detector for detecting the portion of the light transmitted through the tissue of the subject;

c. providing at least one detector for detecting a physical dimension of the tissue of the subject near or at the location of the at least one light source;

d. measuring the absorbance of the light at the first wavelength by the tissue at both the systolic and diastolic phases of the pulsatile flow;

e. measuring the absorbance of the light at the second wavelength by the tissue at both the systolic and diastolic phases of the pulsatile flow;

f. determining the rate of change over time of absorbance of light of the first wavelength during pulsatile flow;

g. determining the rate of change over time of absorbance of light of the second wavelength during pulsatile flow;

h. determining the rate of change over time in physical dimension during pulsatile flow at or near the location of the at least one light source;

i. calculating a ratio of the rate of change in light absorbance over time divided by the rate of change over time in physical dimension for the first wavelength;

j. calculating a ratio of the rate of change in light absorbance over time divided by the rate of change over time in physical dimension for the second wavelength;

k. calculating the concentration of the blood component in said subject's blood by comparing the results of a formula employing the ratios determined in step i and j as independent variables to the results of the same formula in subjects with known blood component levels.

* * * * *